(12) United States Patent
Fujita et al.

(10) Patent No.: US 9,880,182 B2
(45) Date of Patent: Jan. 30, 2018

(54) AUTOMATIC ANALYZER

(71) Applicant: HITACHI HIGH-TECHNOLOGIES CORPORATION, Tokyo (JP)

(72) Inventors: Hiroki Fujita, Tokyo (JP); Toshiharu Suzuki, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 43 days.

(21) Appl. No.: 14/895,030

(22) PCT Filed: Jul. 8, 2014

(86) PCT No.: PCT/JP2014/068215
§ 371 (c)(1),
(2) Date: Dec. 1, 2015

(87) PCT Pub. No.: WO2015/005356
PCT Pub. Date: Jan. 15, 2015

(65) Prior Publication Data
US 2016/0146846 A1    May 26, 2016

(30) Foreign Application Priority Data
Jul. 9, 2013 (JP) .................. 2013-143851

(51) Int. Cl.
*G01N 35/04* (2006.01)
*G01N 35/00* (2006.01)

(52) U.S. Cl.
CPC . *G01N 35/00732* (2013.01); *G01N 35/00663* (2013.01); *G01N 35/04* (2013.01);
(Continued)

(58) Field of Classification Search
CPC ..... G01N 2035/0465; G01N 35/00732; G01N 2035/00891; G01N 2035/00316; G01N 2035/00435
See application file for complete search history.

(56) References Cited

U.S. PATENT DOCUMENTS

2008/0056939 A1    3/2008  Awata et al.
2010/0104478 A1    4/2010  Kondou
(Continued)

FOREIGN PATENT DOCUMENTS

EP    2 053 410 A2    4/2009
EP    2333563 A1    6/2011
(Continued)

OTHER PUBLICATIONS

International Preliminary Report on Patentability received in corresponding International Application No. PCT/JP2014/068215.
(Continued)

*Primary Examiner* — P. Kathryn Wright
(74) *Attorney, Agent, or Firm* — Mattingly & Malur, PC

(57) ABSTRACT

An automatic analysis device is provided with a reagent container disk, a reagent loader (6), a reagent loader position sensor, an RFID antenna, a memory unit, a reagent loading switch (26), and reagent load position LEDs (21-25). The reagent loader (6) has a plurality of slots for inserting reagent containers (4) and moves between the outside and the reagent container disk. The reagent load position LEDs (21-25) display determination results for each slot indicating whether the reagent accommodated in the reagent container inserted into the slot or the slot can be used on the basis of the presence of a reagent container in the slot and the reagent state of the inserted reagent or the state of the slot.

17 Claims, 11 Drawing Sheets

(52) U.S. Cl.
CPC ........... *G01N 2035/00316* (2013.01); *G01N 2035/00435* (2013.01); *G01N 2035/00673* (2013.01); *G01N 2035/00891* (2013.01); *G01N 2035/0403* (2013.01); *G01N 2035/0443* (2013.01); *G01N 2035/0465* (2013.01); *G01N 2035/0467* (2013.01); *G01N 2035/0491* (2013.01)

(56) References Cited

U.S. PATENT DOCUMENTS

| | | | | |
|---|---|---|---|---|
| 2012/0156788 | A1* | 6/2012 | Kim | G01N 35/00722 436/50 |
| 2012/0301359 | A1* | 11/2012 | Kraemer | G01N 35/04 422/64 |
| 2013/0130369 | A1* | 5/2013 | Wilson | B01L 3/5085 435/289.1 |
| 2014/0295562 | A1* | 10/2014 | Wakamiya | G01N 35/04 436/48 |

FOREIGN PATENT DOCUMENTS

| | | |
|---|---|---|
| EP | 2 520 939 A2 | 11/2012 |
| JP | 09-211004 A | 8/1997 |
| JP | 10-096733 A | 4/1998 |
| JP | 2008-020335 A | 1/2008 |
| JP | 4659707 B2 | 3/2011 |
| JP | 2012-189611 A | 10/2012 |
| JP | 2013-019823 A | 1/2013 |
| JP | 2013-500489 A | 1/2013 |
| JP | 2013-127487 A | 6/2013 |
| WO | WO 2011012657 A1 * | 2/2011 ............ G01N 35/04 |
| WO | WO 2012012779 A1 * | 1/2012 ............ B01L 3/50825 |

OTHER PUBLICATIONS

International Search Report of PCT/JP2014/068215.
Extended European Search Report received in corresponding European Application No. 14823586.4 dated Mar. 23, 2017.

* cited by examiner

[Fig. 1]
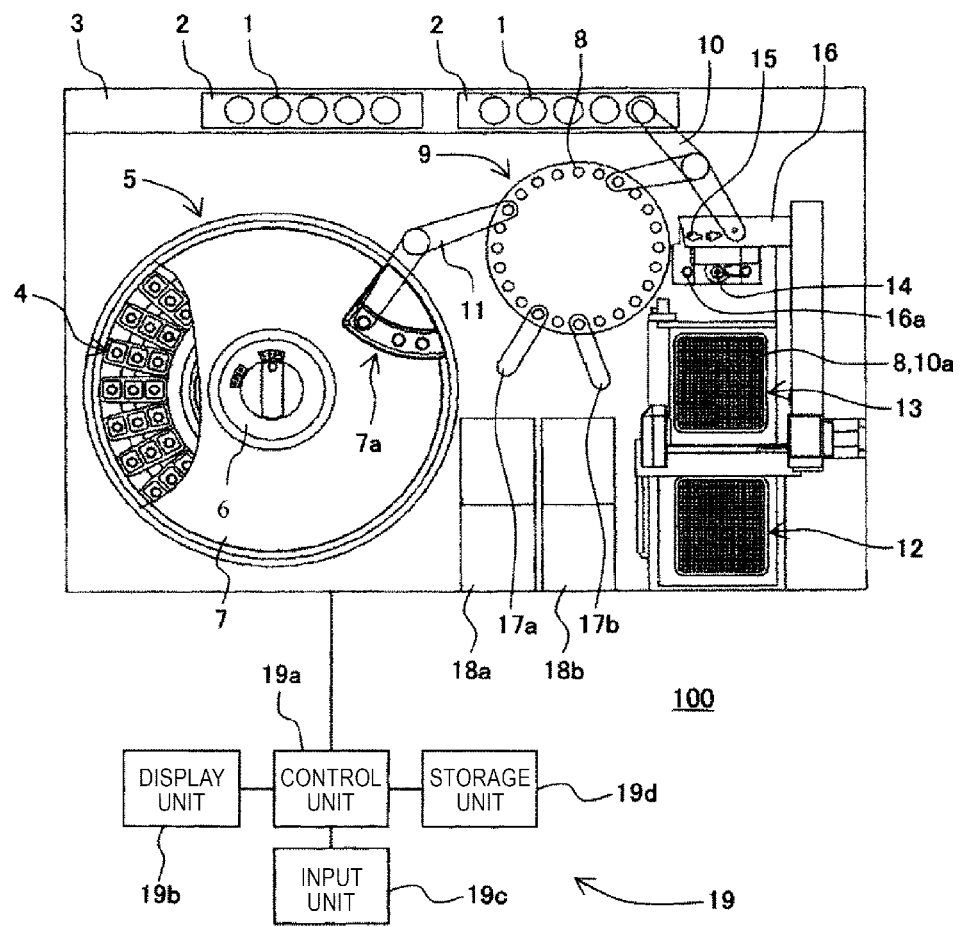

[Fig. 2]
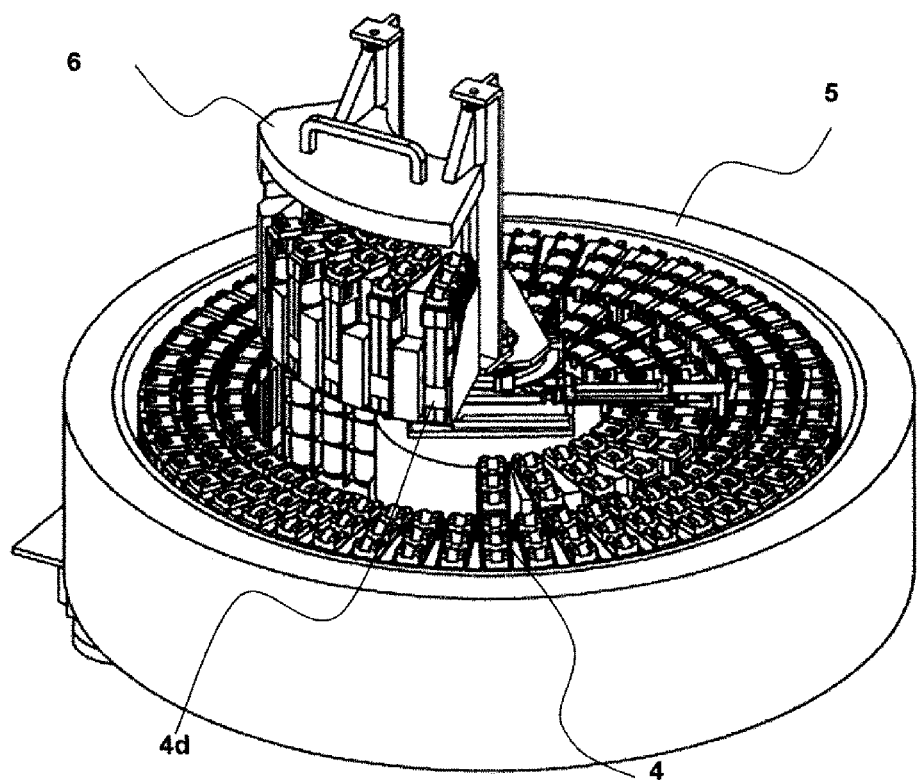

[Fig. 3]
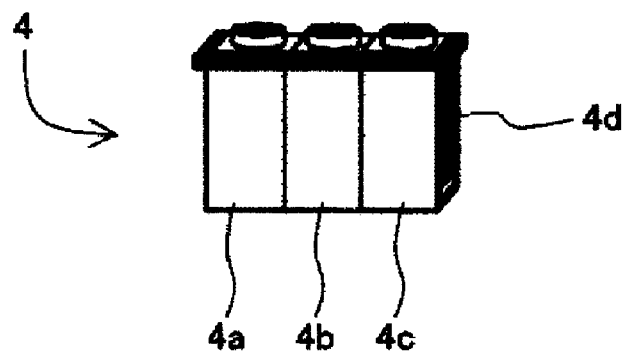
[Fig. 4]
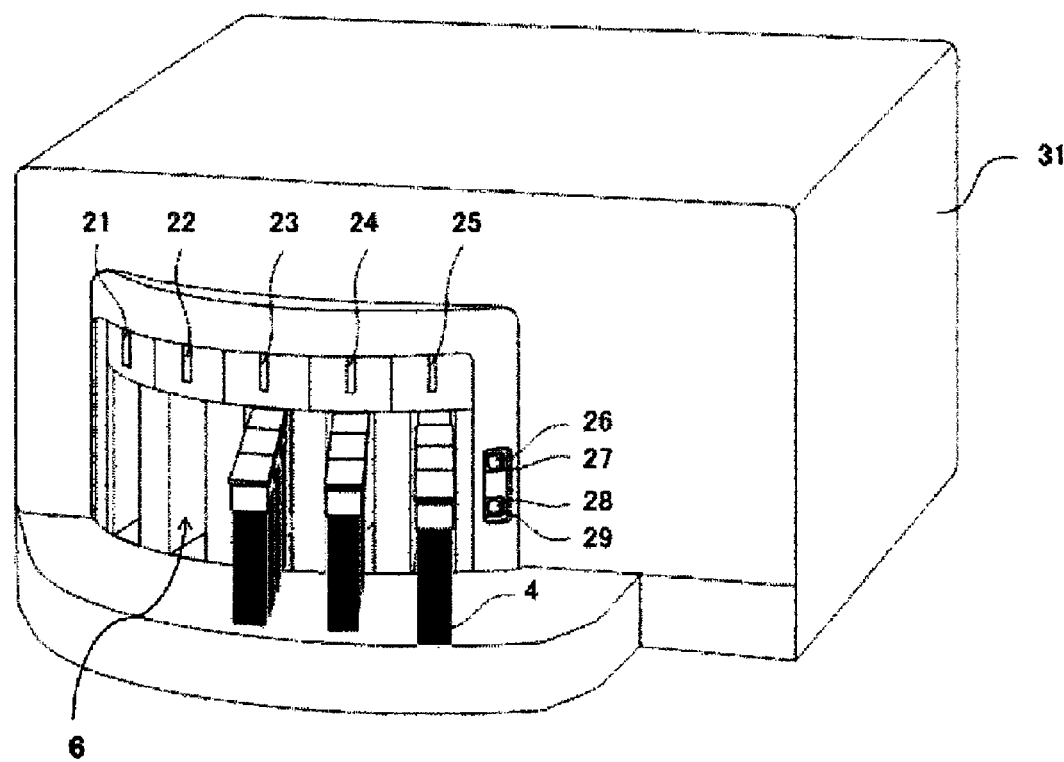

[Fig. 5]
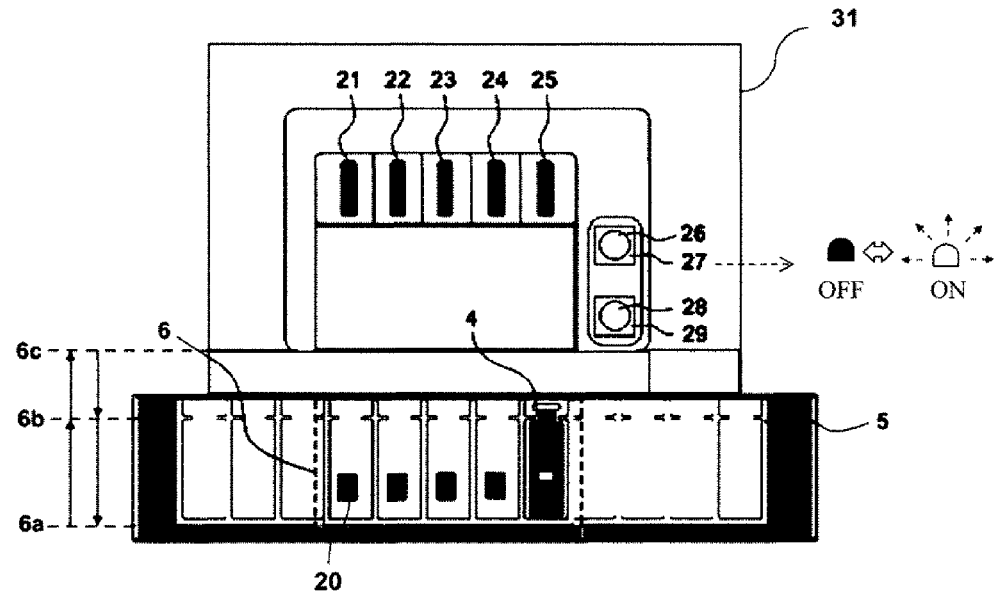
[Fig. 6]
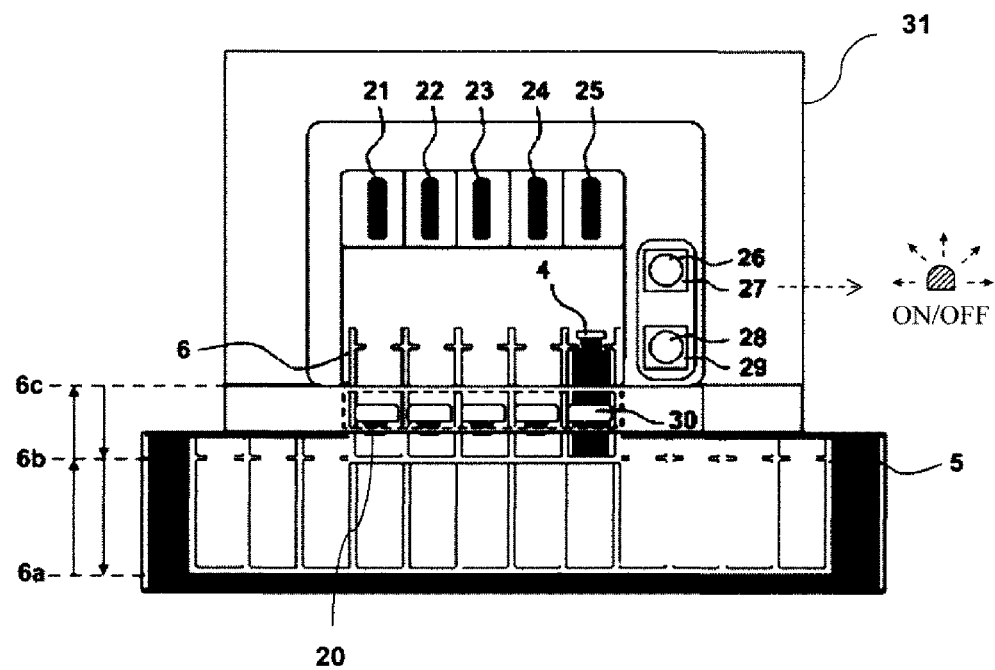

[Fig. 7]
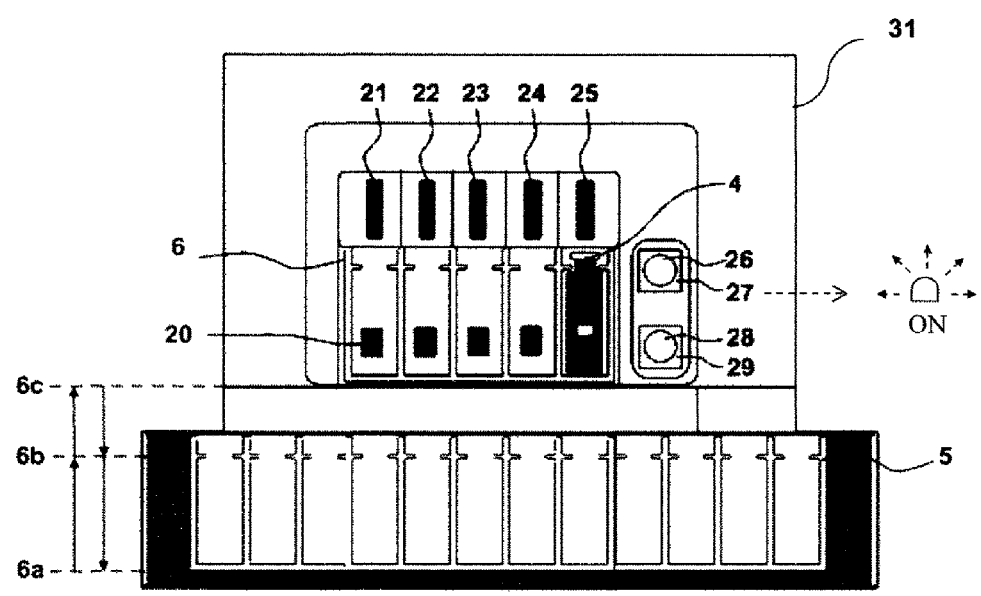

[Fig. 8]
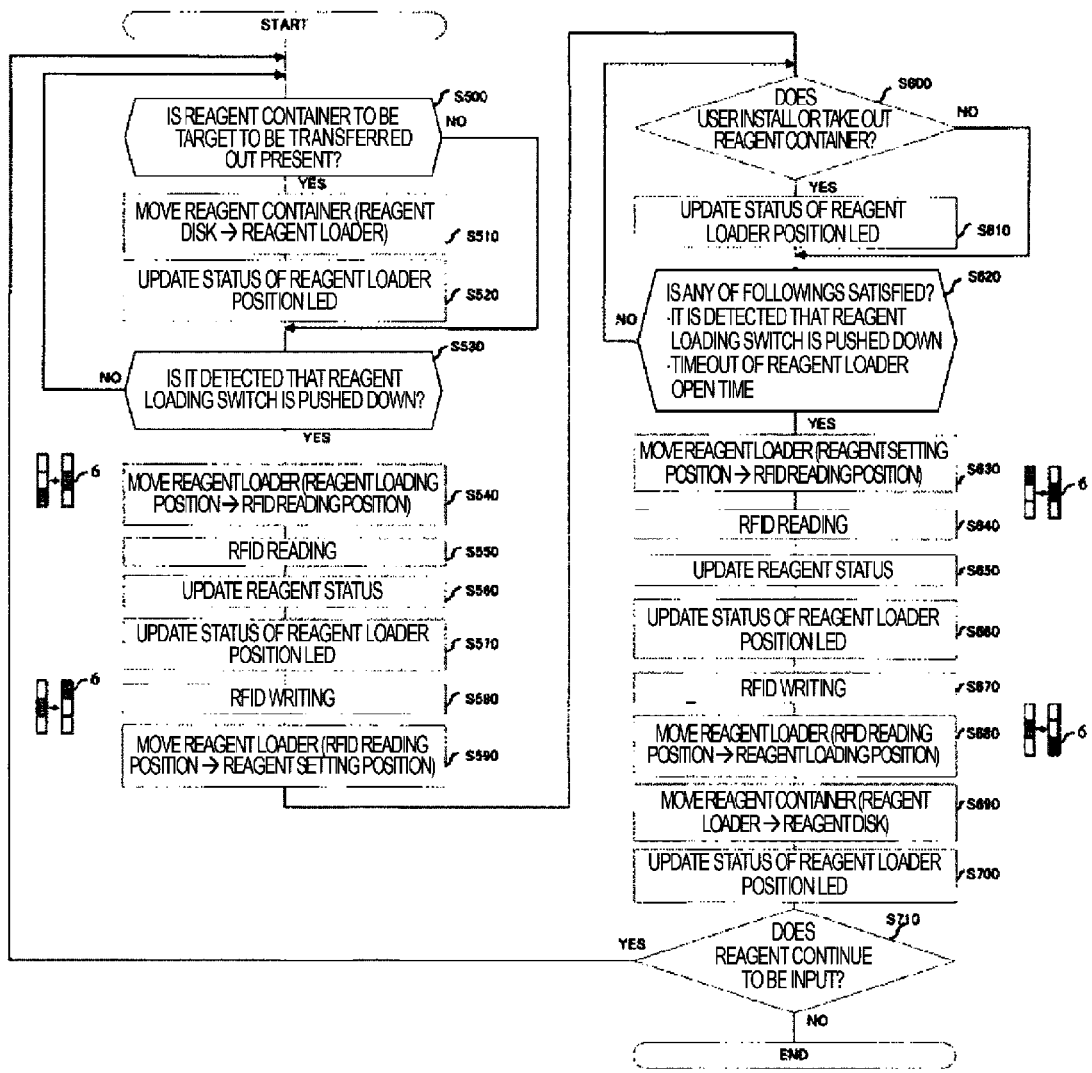

[Fig. 9]
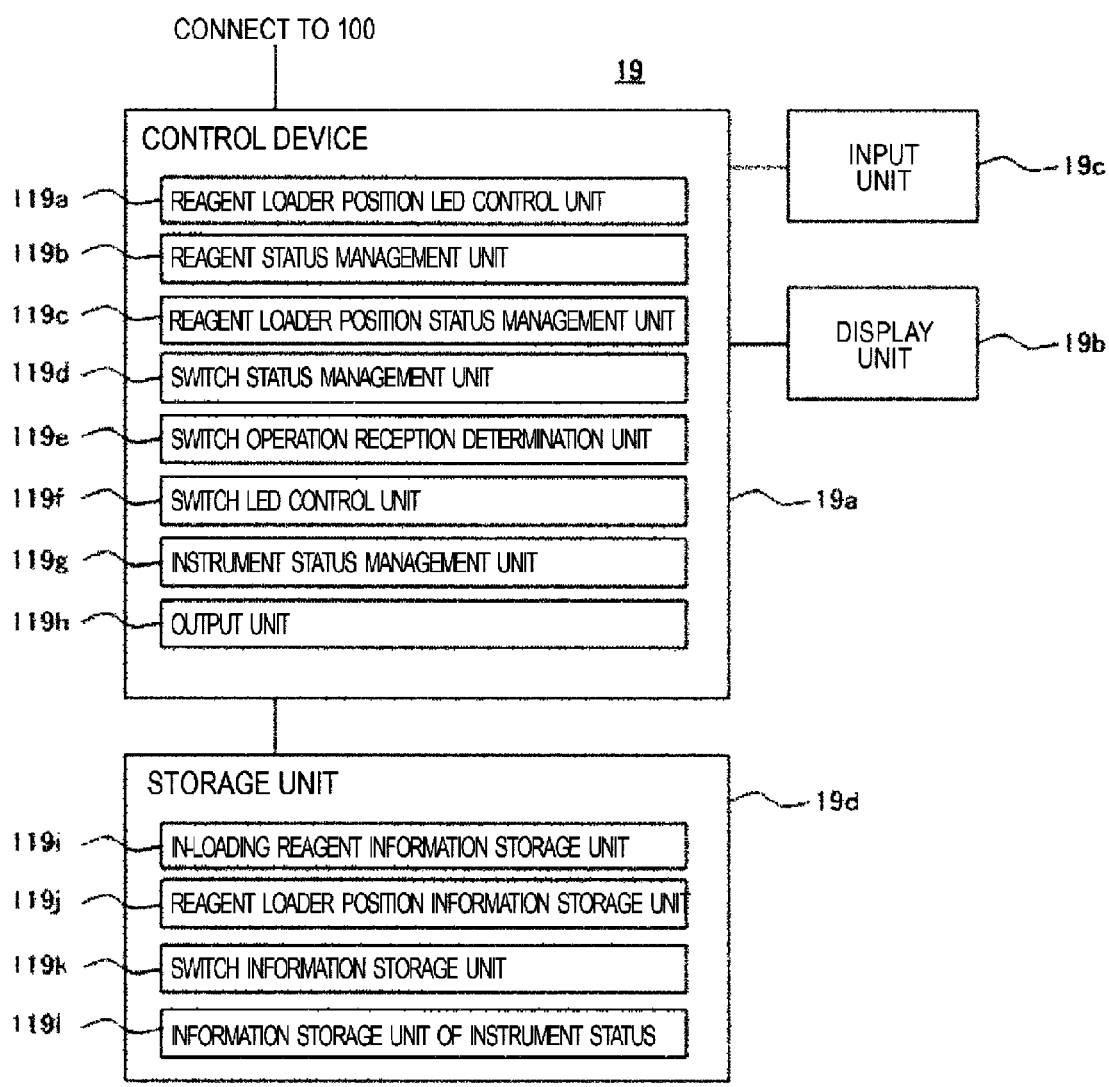

[Fig. 10]
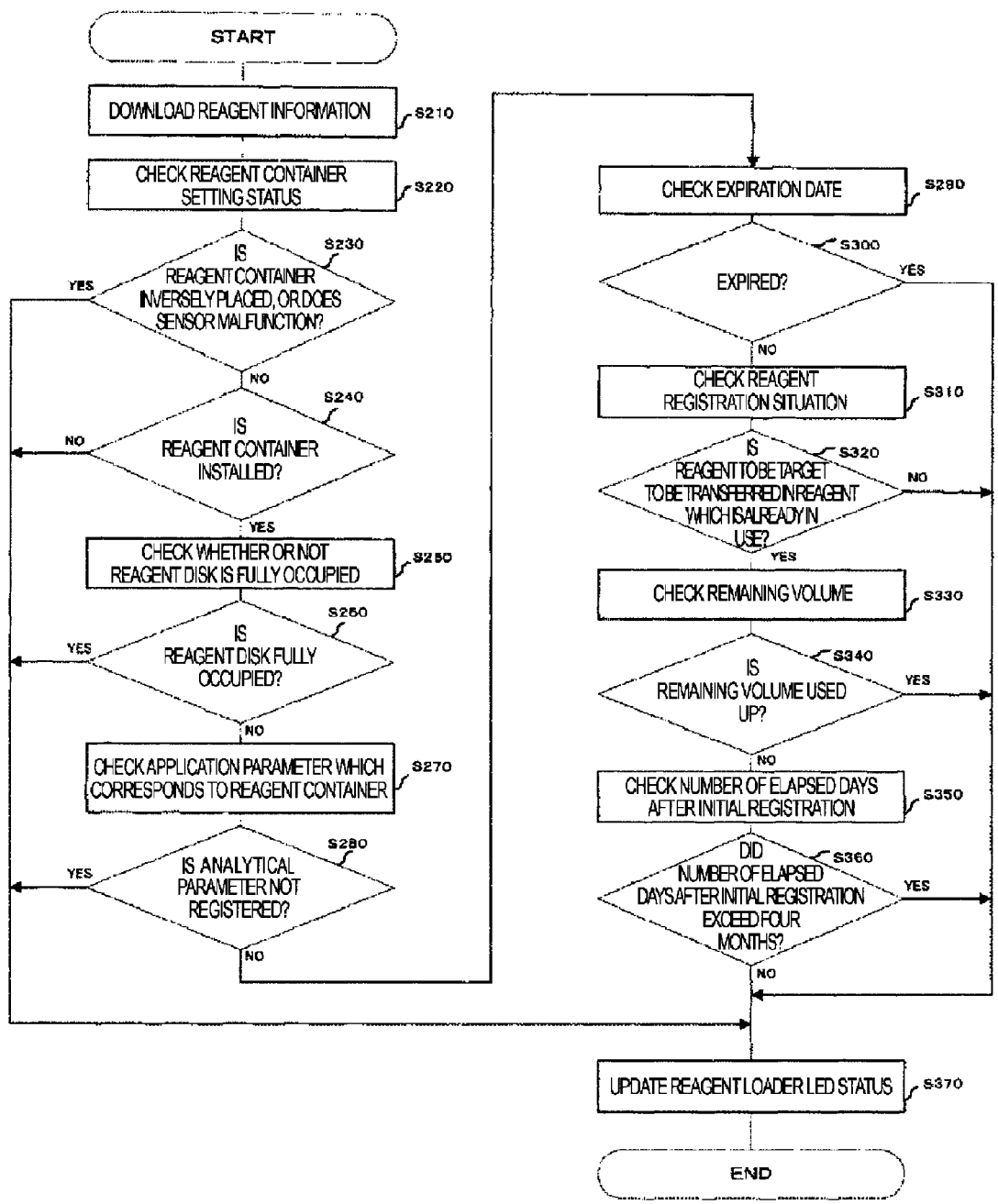

[Fig. 11]
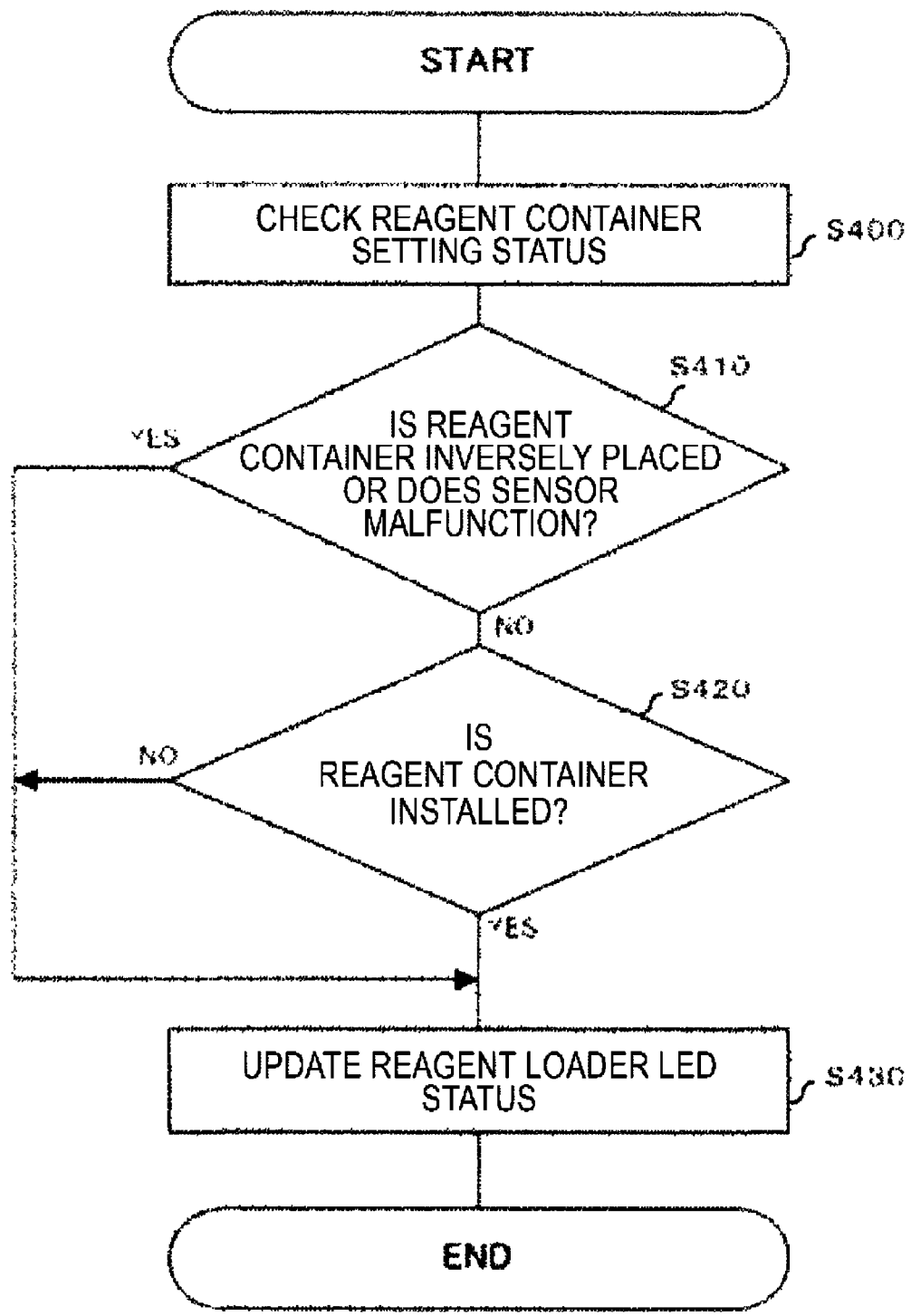

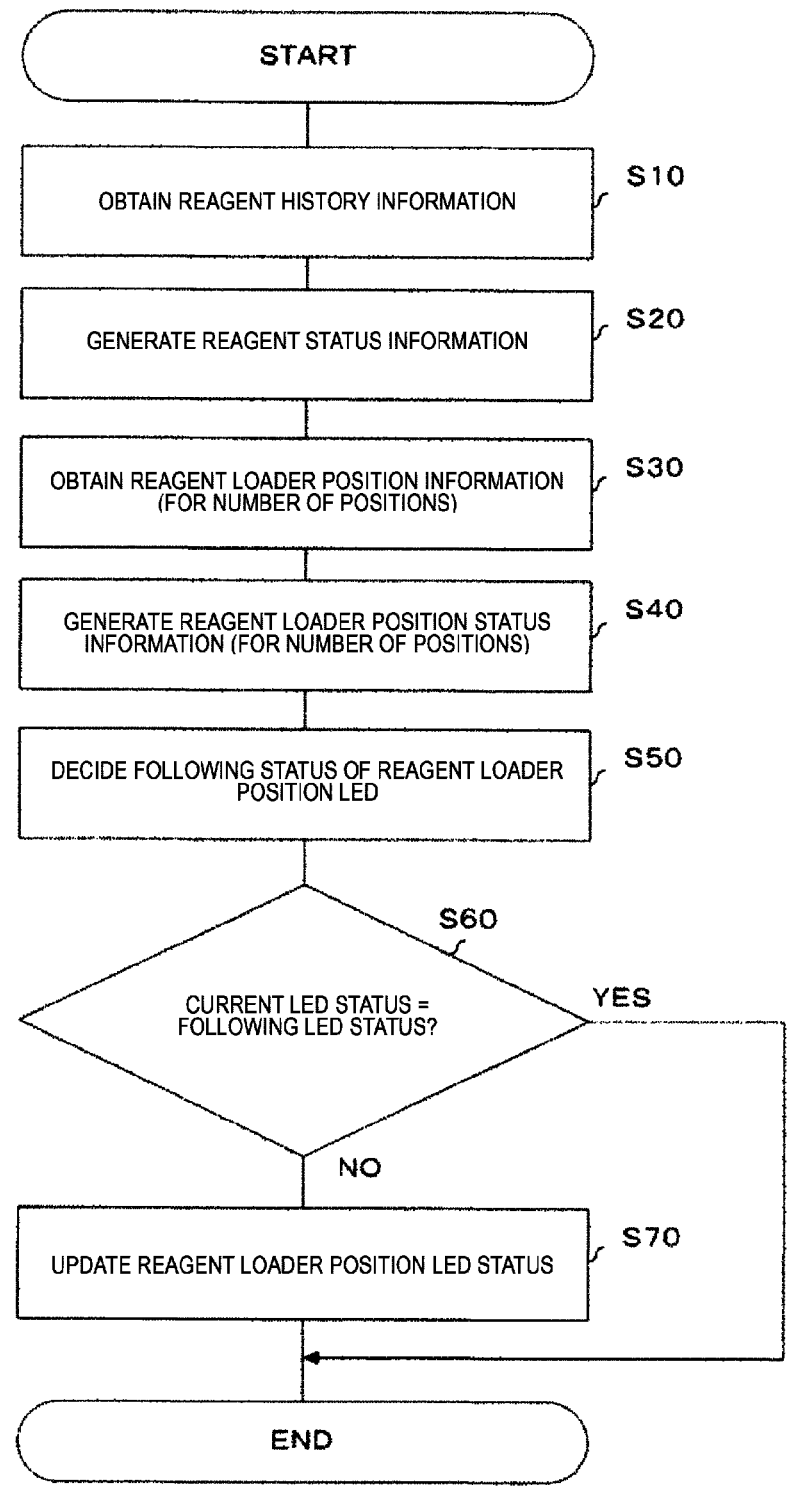
[Fig. 12]

[Fig. 13]
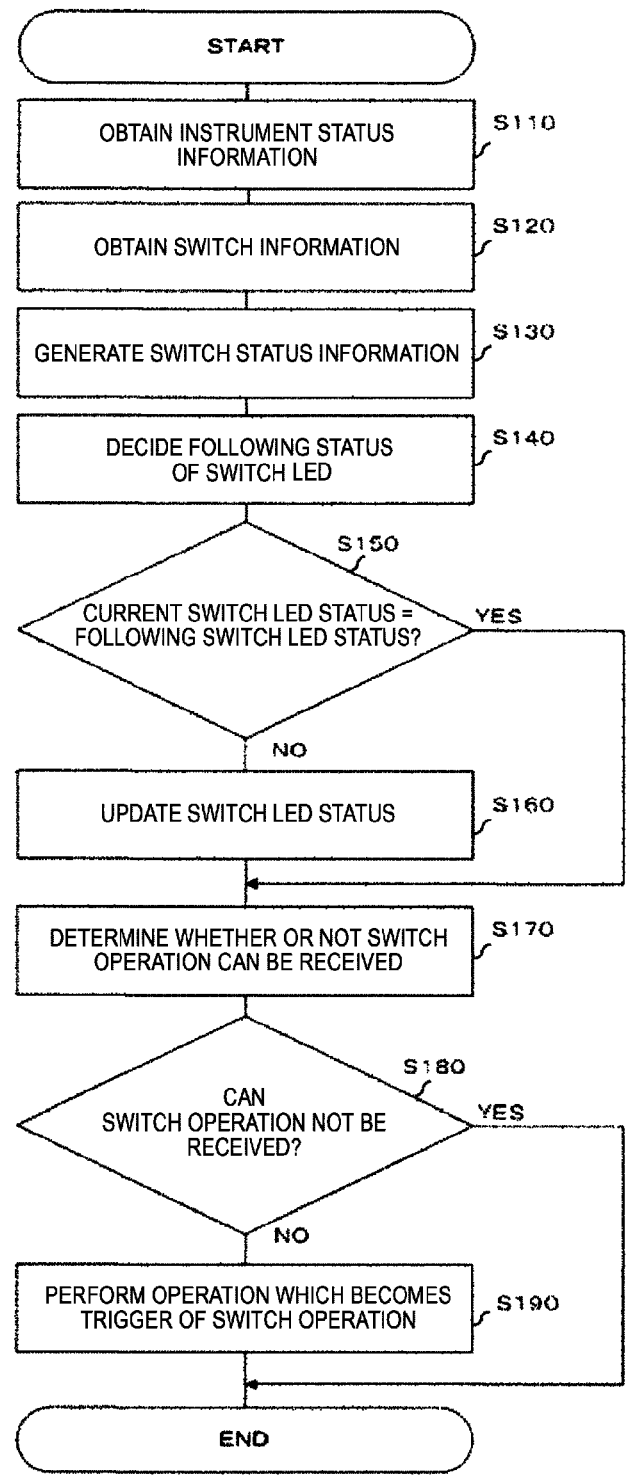

AUTOMATIC ANALYZER

TECHNICAL FIELD

The present invention relates to an automatic analyzer which performs qualitative and quantitative analysis of a biological sample, such as blood or urine.

BACKGROUND ART

An automatic analyzer performs qualitative and quantitative analysis by adding a reagent which specifically reacts to a specific component included in a biological sample, such as blood or urine, making the reagent react, and measuring absorbance or the amount of luminescence of a reaction mixture.

As such an automatic analyzer, an automatic analyzer provided with a reagent loading procedure for loading a plurality of reagents, including display means for displaying information of a loading position of the reagent, information of a remaining volume of the reagent, information of the reagent expiration date, information of the duration time of calibration, and information of the effective period of time for quality control on the same screen, regarding the reagent loaded on the reagent loading procedure, in which, in the display means, information of a mounting position of the reagent displays a position of the reagent which is disposed in the reagent loading procedure corresponding to a physical position, and the display means identifies and displays the information of a remaining volume of the reagent, the information of the reagent expiration date, the information of the duration time of calibration, and the information of the effective period of time for quality control following classification determined in advance, is known (for example, refer to PTL 1).

CITATION LIST

Patent Literature

PTL 1: Japanese Patent No. 4659707

SUMMARY OF INVENTION

Technical Problem

In recent years, in a large hospital or in a large-scale laboratory, an automatic analyzer which integrates different types of analysis, such as clinical chemistry or immunoassay, into one system has been mainly employed. In the integrated system which is configured of different types of plural analytical modules, by integrating a plurality of tasks into one system, test efficiency is improved, for example, a flow of sample or work can be integrated.

Meanwhile, not being limited to the above-described system, an operation of a user with respect to the automatic analyzer is basically performed by a control device, such as a personal computer (PC). However, in order to replenish a reagent container, a sample rack which is used in analysis, a reaction cell, or consumables, such as detergent, a physical operation of the user with respect to the instrument is necessary. In particular, the user performs work of installing and taking out the reagent container while confirming the status of the reagent by a display unit of the control device. For example, when three types of containers, such as a reagent container A in which the reagent has expired, a reagent container B with a normal status, and a reagent container C in which foam is detected during the analysis, are taken out of the instrument at the same time, it is necessary for the user to confirm the information of the reagent containers A to C to be taken out in advance by the display unit (screen) of the control device.

However, in the automatic analyzer which connects the plurality of analytical modules to each other similar to the above-described integrated system, the distance from the control device to the analytical module increases as the number of connected analytical modules increases. For this reason, there is a problem that operability deteriorates when the user performs the work of installing and taking out the reagent container while confirming the information of the reagent container.

An object of the present invention is to provide an automatic analyzer in which operability can be improved when a user performs work of installing and taking out a reagent container while confirming information of the reagent container.

Solution to Problem

In order to achieve the above-described object, there is provided an automatic analyzer including: a reagent container retain unit which retains a plurality of reagent containers; a reagent loader which has a plurality of slots to which the reagent containers are inserted, and moves between the outside and the reagent container retain unit; a sensor which detects the presence or the absence of the reagent container in each slot; a reader which reads identification information that identifies a reagent accommodated in the reagent container inserted in the slot; a storage unit which stores the identification information and reagent status information illustrating the status of the reagents in association with each other; a first switch which moves the reagent loader; and a display unit which displays a determination result of whether or not the reagent accommodated in the reagent container inserted to the slot or the corresponding slot can be used, based on the presence or the absence of the reagent container, the status of the inserted reagent, or the status of the corresponding slot in each slot, in each slot.

Advantageous Effects of Invention

According to the present invention, it is possible to improve operability when a user performs work of installing and taking out a reagent container while confirming information of the reagent container. Problems, configurations, and effects except for those described above will be apparent by the following description of an embodiment.

BRIEF DESCRIPTION OF DRAWINGS

FIG. 1 is a configuration view of an automatic analyzer according to an embodiment of the present invention.

FIG. 2 is a view illustrating a configuration of a peripheral unit of a reagent disk which is used in the automatic analyzer according to the embodiment of the present invention.

FIG. 3 is a configuration view of a reagent container which is used in the automatic analyzer according to the embodiment of the present invention.

FIG. 4 is a view illustrating a configuration of a peripheral unit of a reagent loader which is used in the automatic analyzer according to the embodiment of the present invention.

FIG. 5 is a view illustrating a stop position of the reagent loader when transferring the reagent container into the reagent disk from the reagent loader, and an associated mechanism thereof, in the automatic analyzer according to the embodiment of the present invention.

FIG. 6 is a view illustrating a stop position of the reagent loader when reading out information of an RFID tag of the reagent container and writing the information of the RFID tag, and an associated mechanism thereof, in the automatic analyzer according to the embodiment of the present invention.

FIG. 7 is a view illustrating a stop position of the reagent loader when a user transfers the reagent container in and out, and an associated mechanism thereof, in the automatic analyzer according to the embodiment of the present invention.

FIG. 8 is a flowchart illustrating processing of transferring the reagent container out of the reagent disk and into the reagent disk, in the automatic analyzer according to the embodiment of the present invention.

FIG. 9 is a view illustrating a function of a control device which is used in the automatic analyzer according to the embodiment of the present invention.

FIG. 10 is a flowchart illustrating processing of updating reagent status information when transferring the reagent in, in the automatic analyzer according to the embodiment of the present invention.

FIG. 11 is a flowchart illustrating processing of updating the reagent status information when transferring the reagent out, in the automatic analyzer according to the embodiment of the present invention.

FIG. 12 is a flowchart illustrating processing of controlling a reagent loader position LED, in the automatic analyzer according to the embodiment of the present invention.

FIG. 13 is a flowchart illustrating processing of a flow of control of switch LEDs and switch operations when operating each switch, in the automatic analyzer according to the embodiment of the present invention.

DESCRIPTION OF EMBODIMENTS

Hereinafter, using FIGS. 1 to 13, a configuration and operations of an automatic analyzer 100 according to an embodiment of the present invention will be described. For example, the automatic analyzer 100 performs different types of analysis, such as clinical chemistry or immunoassay, in one system. In addition, in FIGS. 1 to 13, the same parts are given the same reference numerals.

First, using FIG. 1, the entire configuration of the automatic analyzer 100 according to the embodiment of the present invention will be described. FIG. 1 is a configuration view of the automatic analyzer 100 according to the embodiment of the present invention.

The automatic analyzer 100 includes a sample rack 2, a rack transfer line 3, a reagent disk 5, a reagent loader 6, an incubator disk 9, a sample pipetting nozzle 10, a reagent pipetting nozzle 11, a reaction cell & sample pipetting tip unloading unit 12, a replacement/replenishment reaction cell & sample pipetting tip unloading unit 13, a reaction cell mixing mechanism 14, a disposal hole 15, a transfer mechanism 16, a nozzle 17 (17a and 17b), an detection unit 18 (18a and 18b), and a control device 19. In addition, if the present invention can be realized, an automatic analyzer having another configuration may be employed, and an automatic analyzer having a configuration in which a plurality of reagent containers can be retained may be employed.

The sample rack 2 unloads a plurality of sample containers 1 which accommodates a biological sample (hereinafter, referred to as a sample), such as blood or urine. The rack transfer line 3 transfers the sample rack 2.

The reagent disk 5 (reagent container retain unit) is covered with a reagent disk cover 7, unloads a plurality of reagent containers 4 which accommodates various reagents to be used in analyzing the sample, and keeps the reagent containers 4 warm. In the reagent disk 5, a reagent cap open mechanism (not illustrated) which opens the reagent container 4 is provided. In addition, the reagent disk 5 is not limited to a disk type, and may be a serial type in which the reagent containers 4 are disposed in one or more rows.

The reagent loader 6 is provided in an inner circumferential unit of the reagent disk 5, the reagent container 4 is transferred to the reagent disk 5 from the outside when installing the reagent container 4, and the reagent container 4 is transferred to the outside from the reagent disk 5 when taking the reagent container 4 out. A configuration of the reagent loader 6 will be described in detail later using FIG. 2.

The incubator disk 9 unloads a plurality of reaction cells 8 for mixing the sample and the reagent with each other. The sample pipetting nozzle 10 pipettes the sample to the reaction cell 8 of the incubator disk 9 from the sample container 1 by rotary drive or vertical drive and an aspirating/discharging operation.

The reagent pipetting nozzle 11 pipettes the reagent to the reaction cell 8 of the incubator disk 9 from the reagent container 4 by the rotary drive or vertical drive and the aspirating/discharging operation, via a reagent disk cover opening unit 7a provided in the reagent disk cover 7. The reaction cell mixing mechanism 14 mixes a reaction mixture accommodated in the reaction cell 8.

The reaction cell & sample pipetting tip unloading unit 13 unloads the plurality of reaction cells 8 and a sample pipetting tip 10a which have not been used. The reaction cell & sample pipetting tip unloading unit 12 is on standby for replacement/replenishment. The disposal hole 15 is a hole for disposing of the sample pipetting tip 10a and the reaction cell 8 which have already been used.

The transfer mechanism 16 grasps and transfers the sample pipetting tip 10a and the reaction cell 8. Specifically, the transfer mechanism 16 is provided to be movable in the X-axis, Y-axis, and Z-axis directions (not illustrated). The transfer mechanism 16 transfers the reaction cell 8 unloaded in the reaction cell & sample pipetting tip unloading unit 13 to the incubator disk 9, disposes of the reaction cell 8 which has already been used to the disposal hole 15, or transfers the sample pipetting tip 10a which has not been used to a tip attachment position 16a.

The nozzles 17a and 17b are respectively sent to the detection units 18a and 18b by aspirating the reaction mixture mixed in the reaction cell 8 of the incubator disk 9, by the rotary drive or the vertical drive. The detection units 18a and 18b perform detection processing with respect to the reaction mixture aspirated and sent by the nozzles 17a and 17b, and perform detection of a specific component.

The control device 19 controls the operations of the entire automatic analyzer 100. The control device 19 includes a control unit 19a, a display unit 19b, an input unit 19c, and a storage unit 19d. A configuration of the control device 19 will be described in detail later using FIG. 9.

Next, using FIG. 2, a configuration of a peripheral unit of the reagent disk 5 (reagent container retain unit) which is used in the automatic analyzer 100 according to the embodiment of the present invention will be described. FIG. 2 is a view illustrating a configuration of the peripheral unit of the reagent disk 5 which is used in the automatic analyzer 100 according to the embodiment of the present invention. In FIG. 2, the reagent disk 5, the reagent loader 6, and a peripheral configuration thereof are isolated and illustrated.

The plurality of reagent containers 4 are loaded on the reagent disk 5. The reagent disk 5 includes the reagent loader 6 in the inner circumferential unit (the vicinity of the center of the reagent disk 5) thereof. The reagent loader 6 includes a plurality of slots to which the reagent containers 4 are inserted. In FIG. 2, the reagent loader 6 has a configuration in which five reagent containers 4 can be installed, but is not limited thereto. The reagent loader 6 transfers the reagent container 4 in and out between the outside and the reagent disk 5 by moving in a vertical direction.

In the reagent disk 5, a reader which reads out a sample identification label 4$d$ (RFID tag in the embodiment) provided in the reagent container 4, and sends the identification information to the control unit 19$a$ of the control device 19, is provided. In addition, a barcode label or the like may be used as the sample identification label 4$d$ of the reagent container 4.

In the identification information stored in the sample identification label 4$d$, a reagent identification number (identification code) for identifying the reagent accommodated in the reagent container 4, a test item to which the accommodated reagents correspond, a reagent identification code, a lot number, a sequential number and the like are included.

Next, using FIG. 3, a configuration of the reagent container 4 which is used in the automatic analyzer 100 according to the embodiment of the present invention will be described. FIG. 3 is a configuration view of the reagent container 4 which is used in the automatic analyzer 100 according to the embodiment of the present invention.

Each of the reagent containers 4 is configured of containers 4$a$ to 4$c$ which accommodate the plural types (three in the embodiment) of reagents. In one reagent container 4 (that is, one group of containers 4$a$ to 4$c$), one group of reagents which is necessary in the corresponding test item is accommodated. Examples of the reagent accommodated in each of the containers 4$a$ to 4$c$ of the reagent container 4 include a luminescent labeling reagent including a luminescent label, or a bead reagent including magnetic microparticles.

Next, using FIGS. 4 to 7, a configuration and operations of the reagent loader 6 which is used in the automatic analyzer 100 according to the embodiment of the present invention will be described.

First, using FIG. 4, a configuration of the circumferential unit of the reagent loader 6 which is used in the automatic analyzer 100 according to the embodiment of the present invention will be described. FIG. 4 is a view illustrating the configuration of the circumferential unit of the reagent loader 6 which is used in the automatic analyzer 100 according to the embodiment of the present invention. In FIG. 4, the reagent loader 6 and a circumferential configuration thereof are isolated and illustrated.

In the embodiment, the reagent loader 6 is covered with a reagent unit cover 31. In addition, in FIG. 1 illustrating the configuration of the entire automatic analyzer 100, in order to make it easy to understand the drawing, the reagent unit cover 31 is not illustrated.

In the reagent unit cover 31, reagent loader position LEDs 21 to 25, a reagent loading switch 26, a reagent loading switch LED 27, a timer reset switch 28, and a timer reset switch LED 29, are fixedly provided.

When transferring the reagent container 4 into or out of the reagent loader 6, a user can visually receive information from the reagent loader position LEDs 21 to 25, the reagent loading switch LED 27, and the timer reset switch LED 29, and can give an instruction to the device by using the reagent loading switch 26 and the timer reset switch 28.

The corresponding reagent loader position LEDs 21 to 25 are disposed at each of the positions of the reagent loader 6. The reagent loader position LEDs 21 to 25 have (display) at least three colors for one position.

Each color of the reagent loader position LEDs 21 to 25 represents the status (reagent status) of the reagent installed in the reagent loader 6, and the status (reagent load position status) of a position of the reagent loader 6. In the embodiment, for example, each of three colors is green, yellow, and orange.

Here, green illustrates a reagent status where the reagent container can be used, or a status where the reagent loader position can be used and any reagent container is installed, and yellow illustrates a status where the reagent container temporarily cannot be used as foam or film is detected (film of the reagent generated at a port of the reagent container 4). Orange illustrates a status where the reagent cannot be used because the residual volume is used up or the reagent has expired, or a status where the position of the reagent loader 6 cannot be used because the number of failures in reading out the RFID tag reaches a predetermined limit.

Accordingly, the user can identify the status of the reagent from the reagent loader position LEDs 21 to 25, and the position of the reagent loader 6 at which the reagent container 4 can be installed even without moving to the control device 19 from the front of the analytical module and seeing a screen of the display unit 19$b$.

In addition, in the embodiment, the LED is an example of an indicator, but the invention is not limited to the LED. For example, the reagent status and the position of the reagent loader 6 at which the reagent container 4 can be installed, may be displayed on the display unit, such as a liquid crystal display (LCD) provided on the reagent unit cover 31.

The reagent loading switch 26 is a member for instructing the control unit 19$a$ to start transferring the reagent container 4 in and out by the user. The reagent loading switch 26 switches the ON/OFF status every time the reagent loading switch 26 is pushed down. When the reagent loader 6 raises to a position 6$c$ at which the reagent container 4 is accessible by the user, and when the movement of the reagent container 4 which is a target to be transferred out from the reagent disk 5 to the reagent loader 6 is completed, the reagent loading switch LED 27 is turned on.

When the reagent loading switch LED 27 is turned on, the user can press the reagent loading switch 26. When the user presses the reagent loading switch 26 at the time when the reagent loading switch LED 27 is on, the reagent loading switch LED 27 blinks. The reagent loading switch LED 27 which blinks is turned off after transferring the reagent container 4 in and out is completed (when the reagent loader 6 is at a reagent loading position 6$a$, and the reagent container 4 is moved to the reagent disk 5 from the reagent loader 6).

When the reagent loading switch LED 27 is off or blinks, the instrument does not react even when the user presses the reagent loading switch 26. Accordingly, the user can ascertain timing when the reagent container 4 can be transferred in and out, from the status of the reagent loading switch LED 27 even without moving to the control device 19 from the front of the analytical module and seeing the screen of the display unit 19$b$.

Operations of the timer reset switch 28 and the timer reset switch LED 29 will be described in detail later using FIG. 7.

Next, using FIGS. 5 to 7, the operation of the peripheral unit of the reagent loader 6 which is used in the automatic analyzer 100 according to the embodiment of the present invention will be described.

FIG. 5 is a view illustrating a stop position of the reagent loader 6 when transferring the reagent container 4 into the reagent disk 5 from the reagent loader 6, and an associated mechanism thereof, in the automatic analyzer 100 according to the embodiment of the present invention. In the example of FIG. 5, the reagent loader 6 is stopped at the reagent loading position 6a which is the lowest position in a movable range in the vertical direction.

Here, when the reagent container 4 is not moved to the reagent loader 6 (that is, even when one reagent container 4 is not present in the reagent loader 6), the reagent loading switch LED 27 is turned off. Meanwhile, when the reagent container 4 is moved to the reagent loader 6 (that is, when at least one reagent container 4 is present in the reagent loader 6), the reagent loading switch LED 27 is turned on.

The reagent loader 6 is provided with a sensor on position of reagent loader 20 which detects the presence or the absence of the reagent container 4 in each slot. At the time when the reagent loader 6 is stopped at the reagent loading position 6a, the reagent disk 5 is closed or sealed. The inside of the reagent disk 5 is kept cool at a constant temperature for preventing deterioration of the reagent.

FIG. 6 is a view illustrating a stop position of the reagent loader 6 when reading out the information of the RFID tag of the reagent container 4 and writing the information of the RFID tag, and an associated mechanism thereof, in the automatic analyzer 100 according to the embodiment of the present invention. In the example of FIG. 6, the reagent loader 6 is stopped at the RFID reading position 6b.

Here, when the reagent loader 6 is between the reagent loading position 6a and a reagent setting position 6c, the reagent loading switch LED 27 blinks. In addition, at the time when the reagent loader 6 is stopped at an RFID reading position 6b, the reagent disk 5 is not sealed.

At the RFID reading position 6b, the sensor on position of reagent loader 20 detects the presence or the absence of the reagent container 4. In addition, an RFID antenna 30 reads out the information of the RFID tag of the reagent container 4 which is stopped at the RFID reading position 6b.

FIG. 7 is a view illustrating a stop position of the reagent loader 6 when the user transfers the reagent container 4 in and out, and an associated mechanism thereof, in the automatic analyzer 100 according to the embodiment of the present invention. In the example of FIG. 7, the reagent loader 6 is stopped at the reagent setting position 6c.

Here, when the reagent loader 6 is stopped at the reagent setting position 6c, the reagent loading switch LED 27 is turned on. In addition, at this time, the reagent disk 5 is not sealed.

Next, a case where the reagent loader 6 is moved to the reagent setting position 6c via the RFID reading position 6b from the reagent loading position 6a will be described.

The control unit 19a responds to the reagent loading switch 26 being pushed down at the time when the reagent loading switch LED 27 is on, and operates a driving unit (an actuator or the like) to move the reagent loader 6 to 6c via 6b from the reagent loading position 6a.

When the reagent loader 6 starts moving from the reagent loading position 6a, the control unit 19a monitors (measures) a period of time T (open time) when the reagent container 4 on the reagent disk 5 is in contact with the outside air. In addition, the open time T illustrates a period of time during which the reagent loader 6 is not continuously closed.

When the period of time T during which the reagent container 4 is in contact with the outside air exceeds a certain period of time T1, the control unit 19a generates a beeping sound by using a speaker, and makes the timer reset switch LED 29 blink. Accordingly, a user is notified that a predetermined timeout is close.

Here, when the user presses the timer reset switch 28, the timer reset switch LED 29 is turned off, and a timer which measures the period of time T during which the reagent container 4 is in contact with the outside air is reset.

Accordingly, the user can ascertain the timeout of the duration of being in contact with the outside air inside the reagent disk 5, and can perform an operation corresponding thereto with respect to the automatic analyzer 100 without moving to the control device 19 from the front of the analytical module and seeing the screen of the display unit 19b.

Meanwhile, when the period of time T during which the reagent container 4 is in contact with the outside air exceeds a certain period of time T2 (T2>T1), the control unit 19a operates the driving unit to move the reagent loader 6 to the reagent setting position 6a via 6b from 6c.

As described above, when the reagent loader 6 is stopped at the reagent loading position 6a, the reagent disk 5 is sealed. In addition, the inside of the reagent disk 5 is kept cool at a constant temperature for preventing deterioration of the reagent. However, when the user installs the reagent container 4, the control unit 19a moves the reagent loader 6 to the reagent setting position 6c which is a position where the reagent container 4 is accessible from the outside, from the reagent loading position 6a. For this reason, the reagent loader 6 and the reagent disk 5 are not sealed, and outside air reaches the reagent disk 5.

At this time, in order to keep the temperature inside the reagent disk 5 constant, the contact between the air inside the reagent disk 5 and the outside air should be suppressed, and the control unit 19a automatically moves the reagent loader 6 to the reagent loading position 6a at which outside air is blocked when the certain period of time T2 elapses.

In a case where the user is still installing the reagent container 4 to the reagent loader 6, it is possible to extend the period of time by using the timer reset switch 28. As the user presses the timer reset switch 28, the control unit 19a resets the timer which measures the period of time T during which the reagent container 4 is in contact with the outside air. In this manner, in order to reset the timer, it is not necessary for the user to move to the control device 19 from the front of the analytical module, and to perform the operation from the screen of the display unit 19b. In the embodiment, by pressing the switch which is close to the hand while installing the reagent container 4, the user can avoid a risk that the reagent loader 6 starts to move.

Next, using FIG. 8, a processing flow of transferring the reagent container 4 in and out of the reagent disk 5 will be described. FIG. 8 is a flowchart illustrating the processing of transferring the reagent container 4 in and out of the reagent disk 5, in the automatic analyzer 100 according to the embodiment of the present invention.

First, the control unit 19a determines (confirms) whether or not the reagent container 4 to be a target to be discharged is present (step S500). When the reagent container 4 is present (step S500; YES), the control unit 19a moves the reagent container 4 to the reagent loader 6 from the reagent disk 5 (step S510), the reagent loader position LEDs 21 to 25 which are the movement destinations are turned on to colors corresponding to the reagent statuses (step S520). Each reagent status is obtained from reagent history information which is stored in an in-loading reagent information storage unit 119$i$ (will be described in detail later) which is in the storage unit of the control device, and controls the display of the reagent loader position LEDs 21 to 25 based on the reagent status information. The display of the reagent loader position LEDs 21 to 25 at this time, illustrates the reagent status of the reagent container 4 which is installed at the position on the reagent loader 6.

As described above, in the embodiment, correspondence of the colors of the reagent loader position LEDs 21 to 25 and the reagent status of each reagent container 4 when transferring the reagent container out is turned on as a green color when the reagent status information indicates a normal status, as a yellow color in a status where the reagent status information indicates that it temporarily cannot be used, and as an orange color in a status where the reagent status information indicates that it can by no means (permanently) be used.

When the reagent container 4 to be a target to be transferred out is not present (step S500; NO), the processing of the control unit 19$a$ proceeds to step 530. At this time, steps S510 and S520 are not performed.

Next, the control unit 19$a$ determines whether or not it is detected that the reagent loading switch 26 is pushed down (step S530).

When it is detected that the reagent loading switch 26 is pushed down (step S530; YES), the processing of the control unit 19$a$ proceeds to step S540. Meanwhile, when it is detected that the reagent loading switch 26 is not pushed down (step S530; NO), the processing of the control unit 19$a$ returns to step S500.

When it is detected that the reagent loading switch 26 is pushed down (step S530; YES), the control unit 19$a$ moves the reagent loader 6 to the RFID reading position 6$b$ from the reagent loading position 6$a$ (step S540). After the reagent loader 6 is stopped at the RFID reading position 6$b$, the control unit 19$a$ performs RFID reading of the reagent container 4 by using the RFID antenna 30 (step S550). Here, the physical presence or absence of the reagent container is determined based on the reading result of the RFID.

After the RFID reading ends, the control unit 19$a$ updates the reagent status information based on the presence or the absence of the reagent container 4 (step S560). The update of the reagent status information while transferring the reagent container 4 out will be described later using FIG. 11. When the reagent status information is updated, the control unit 19$a$ updates the status of the reagent loader position LED following the reagent status information (step S570). At this time, the display of the reagent loader position LEDs 21 to 25 changes to each color according to the reagent status.

When the status of each of the reagent loader position LEDs 21 to 25 is updated, the control unit 19$a$ performs RFID writing by using the RFID antenna 30 (step S580). After the RFID writing ends, the control unit 19$a$ moves the reagent loader 6 to the reagent setting position 6$c$ from the RFID reading position 6$b$ (step S590).

After the movement of the reagent loader 6 ends, the control unit 19$a$ determines whether a new reagent container 4 is installed in the reagent loader 6 by the user, or the reagent container on the reagent loader 6 is taken out by the user (step S600). When the condition of step S600 is satisfied (step S600; YES), the control unit 19$a$ updates the status of the reagent loader position LED (step S610). Specifically, in order to allow the user to judge whether or not the reagent container 4 is properly installed to the reagent loader 6, the reagent loader position LEDs 21 to 25 are turned on as green when the sensor on position of reagent loader 20 detects the installation of the reagent container. When the LED is not turned on as green regardless of the installation of the reagent container, the user can immediately judge an installation defect by seeing the reagent loader position LED. In addition, when the reagent container is taken out by the user, the LEDs 21 to 25 are turned off.

Meanwhile, when the condition of step S600 is not satisfied (step S600; NO), the processing of the control unit 19$a$ proceeds to step S620. In this case, step S610 is not performed. Accordingly, the processing of transferring the reagent container out ends.

Next, the processing of transferring the reagent container in is performed. The control unit 19$a$ determines whether it is detected that the reagent loading switch 26 is pushed down, or that the open time of the reagent loader 6 has timed out (step S620). When it is detected that the reagent loading switch 26 is pushed down, or that the open time of the reagent loader 6 has timed out (step S620; YES), the processing of the control unit 19$a$ proceeds to step S630.

After detecting that the reagent loading switch 26 is pushed down, or that the open time of the reagent loader 6 has timed out, the control unit 19$a$ moves the reagent loader 6 to the RFID reading position 6$b$ from the reagent setting position 6$c$ (step S630). After the movement of the reagent loader 6 ends, the control unit 19$a$ performs the RFID reading of the reagent container installed at the position of a reagent loader mechanism (reagent loader 6) by using the RFID antenna 30 (step S640).

After the RFID reading ends, the control unit 19$a$ updates the reagent status information (step S650). The update of the reagent status information while transferring the reagent in will be described later using FIG. 10. When the reagent status information is updated, the status of the reagent loader position LED is updated following the reagent status information (step S660). At this time, the display of the reagent loader position LEDs 21 to 25 changes to each color according to the reagent status information.

In the embodiment, the correspondence of the colors of the reagent loader position LEDs 21 to 25 and the reagent status information of each reagent container 4 when transferring the reagent container in is turned on as green in a normal status, blinks in yellow in a status where the reagent status information indicates that it temporarily cannot be used, and is turned on as orange in a status where the reagent status information indicates that it can by no means (permanently) be used, as described above. Regarding the status where the reagent status information temporarily cannot be used, and the status where the reagent status information can by no means be used, by changing a control method by blinking when transferring in and by turning on when transferring out, the user can ascertain that an abnormality is detected in either process of transferring in and transferring out.

When the status of the reagent loader position LEDs 21 to 25 is updated, the control unit 19$a$ performs the RFID writing by using the RFID antenna 30 (step S670). In the step, the information (information which allows the start of use of the reagent, or reagent filling volume information) which is necessary in starting the use of the reagent container that is newly transferred in is written. When the writing is not necessary, the step may be skipped. After the RFID writing ends, the control unit 19$a$ moves the reagent loader 6 to the reagent loading position 6*a* from the RFID reading position 6*b* (step S680). After the movement of the reagent loader 6 ends, the control unit 19*a* transfers the reagent container 4 into the reagent disk 5 from the reagent loader 6 (step S690).

When the movement of the reagent container 4 to the reagent disk 5 from the reagent loader 6 ends, the control unit 19*a* turns off the reagent loader position LED which corresponds to the reagent loader position at which the reagent container to be a target to be transferred in is installed among the reagent loader position LEDs 21 to 25 (step S700).

The control unit 19*a* determines whether or not continuation of reagent input is instructed by the user (step S710). When the continuation of the reagent input is instructed by the user (step S710; YES), the processing of the control unit 19*a* returns to step S500. In the other case (step S710; NO), the control unit 19*a* ends the transferring of the reagent in and out.

In this manner, the reagent loader position LEDs 21 to 25 display the determination result illustrating whether or not the reagent accommodated in the reagent container 4 inserted to the slot or the corresponding slot can be used, based on the presence or the absence of the reagent container 4, the status of the inserted reagent (the presence or the absence of an application parameter, expiration date, reagent registration, remaining volume, or the number of days which have elapsed after initial registration), or the status of the slot (inverse placement, sensor malfunction, or reagent disk fully occupied).

Next, using FIG. 9, a function of the control device 19 which is used in the automatic analyzer 100 according to the embodiment of the present invention will be described. FIG. 9 is a view illustrating the function of the control device 19 which is used in the automatic analyzer 100 according to the embodiment of the present invention. The control device 19 controls the operations of the entire automatic analyzer 100.

The control device 19 includes the input unit 19*c* which performs input of information and setting regarding the sample or the test item, the control unit 19*a* which controls the operation of the automatic analyzer 100 and performs the processing of analysis result based on the contents input to the input unit 19*c*, the display unit 19*b* which displays a setting input screen regarding the analysis or the analysis result, and the storage unit 19*d* which stores information regarding the setting about the analysis, the sample, or the reagent, or the analysis result.

The control device 19 performs the control of the transferring of the reagent container 4 in and out or the analysis processing of the sample, based on a program set in advance or the instruction of an operator input by the input unit 19*c* or the like.

As illustrated in FIG. 9, the storage unit 19*d* includes the in-loading reagent information storage unit 119*i*, a reagent loader position information storage unit 119*j*, a switch information storage unit 119*k*, and an information storage unit of instrument status 119*l*.

The in-loading reagent information storage unit 119*i* is a functional block which stores the reagent history information and the identification information of the reagent container 4 in association with each other. Here, the reagent history information is the reagent information of the plurality of reagent containers 4 which are in the middle of being loaded to the reagent disk 5 (reagent container retain unit), and the reagents accommodated in each of the reagent containers 4, and includes at least the reagent status information. In other words, the in-loading reagent information storage unit 119*i* stores the identification information of the reagent container and the reagent status information in association with each other. The identification information of the reagent container 4 is read by a reader (RFID antenna 30) from the individual sample identification label 4*d* of the reagent container 4.

The identification information of the reagent container 4 read by the reader is sent to the storage unit 19*d* via the control unit 19*a*, and is stored in the in-loading reagent information storage unit 119*i*. In addition, when the reagent container 4 which is being loaded on the reagent disk 5 is taken out, the identification information and the reagent history information regarding the reagent container 4 will be removed from the in-loading reagent information storage unit 119*i*.

As illustrated in FIG. 9, the control unit 19*a* includes a reagent loader position LED control unit 119*a*, a reagent status management unit 119*b*, a reagent loader position status management unit 119*c*, a switch status management unit 119*d*, a switch operation reception determination unit 119*e*, a switch LED control unit 119*f*, and an instrument status management unit 119*g*, and an output unit 119*h*.

The reagent loader position LED control unit 119*a* is a functional block which controls the reagent loader position LEDs 21 to 25 according to the reagent status of the reagent containers 4 installed at each reagent loader position of the reagent loader 6. Specifically, the reagent loader position LED control unit 119*a* instructs a change in the status of the reagent loader position LED, based on the reagent status information obtained from the reagent status management unit 119*b*, and the reagent loader position status obtained from the reagent loader position status management unit 119*c*.

The reagent status management unit 119*b* is a functional block which provides the reagent status information illustrating the latest reagent status of the reagent container 4 loaded on the reagent disk 5. When obtaining of the reagent status information is instructed from the reagent loader position LED control unit 119*a*, the reagent status management unit 119*b* obtains the in-loading reagent information from the in-loading reagent information storage unit 119*i*. In addition, the reagent status management unit 119*b* updates the reagent status information based on the obtained in-loading reagent information, and notifies the information to the reagent loader position LED control unit 119*a*. The update of the reagent status information will be described later using FIGS. 10 and 11.

The reagent loader position status management unit 119*c* is a functional block which provides the reagent loader position status information illustrating the status of each position of the reagent loader 6. When obtaining of the reagent loader position status information is instructed from the reagent loader position LED control unit 119*a*, the reagent loader position status management unit 119*c* obtains the reagent loader position information which is information related to each position of the reagent loader mechanism from the reagent loader position information storage unit 119*j*. In addition, the reagent loader position status management unit 119*c* updates the reagent loader position status information based on the obtained reagent loader position information, and notifies the information to the reagent loader position LED control unit 119*a*.

The switch status management unit 119*d* is a functional block which manages the status of the switch, for example, the presence or the absence of the switch operations of the reagent loading switch 26 and the timer reset switch 28. The switch status management unit 119*d* updates the switch status following the switch operation information which is obtained from the switch information storage unit 119*k* and illustrates the switch operations of the reagent loading switch 26 and the timer reset switch 28. In addition, the switch operation information is information illustrating an input status of each switch.

The switch operation reception determination unit 119*e* is a functional block which determines whether or not to perform reception of installing and taking out the reagent container 4 by the operation of the reagent loading switch 26, and extending access time to the reagent container 4 by the operation of the timer reset switch 28.

The switch operation reception determination unit 119*e* determines whether or not to allow the reception of the operations of the reagent loading switch 26 and the timer reset switch 28 according to the current instrument status obtained from the instrument status management unit 119*g* and the switch status obtained from the switch status management unit 119*d*. When the reception of the operations of each switch is allowed, the switch operation reception determination unit 119*e* makes a plan to carry out the processing which uses the operations of each switch as a trigger. Accordingly, the processing corresponding to ON/OFF status of each switch is carried out.

The switch LED control unit 119*f* is a functional block which controls the LEDs of the reagent loading switch 26 and the timer reset switch 28. Based on the determination result regarding the presence or the absence of the switch reception of the switch operation reception determination unit 119*e*, the switch LED control unit 119*f* creates output information to the reagent loading switch LED 27 and the timer reset switch LED 29, and passes the information to the output unit 119*h*.

The output unit 119*h* outputs LED control information with respect to the display unit 19*b*. The display unit 19*b* updates the display of the reagent loading switch LED 27 or the timer reset switch LED 29 based on the LED control information.

Next, by using FIG. 10, a processing flow regarding the update of the reagent status information when transferring the reagent in, in the automatic analyzer 100 according to the embodiment of the present invention, will be described. FIG. 10 is a flowchart illustrating the processing regarding the update of the reagent status information when transferring the reagent in, in the automatic analyzer 100 according to the embodiment of the present invention.

When the reagent loading switch is input by the user, the control unit 19*a* obtains the in-loading reagent information (step S210). Next, the control unit 19*a* starts a setting status check of the reagent container at each position on the reagent loader mechanism by performing reagent container setting status check (step S220).

Based on the result of the reagent container setting status check, the control unit 19*a* determines whether or not the inverse placement of the reagent container 4 on the reagent loader position or malfunction of the RFID reader is detected, from the detection result of the sensor on position of reagent loader 20 and the reading result of the RFID antenna 30 (step S230). When the inverse placement of the reagent container 4 on the reagent loader position or the malfunction of the reader (RFID reader) is detected (step S230; YES), the control unit 19*a* turns on the corresponding LED among the reagent loader position LEDs 21 to 25 in yellow by updating the reagent loader LED status (step S370). This is for illustrating that the reagent container 4 which temporarily cannot be used is present.

Next, when NO is determined in step S230, the control unit 19*a* determines whether or not the reagent container 4 is installed, based on the result of the reagent container setting status check of step S220 (step S240). When it is determined that the reagent container 4 is not installed (step S240; NO), the control unit 19*a* turns off the corresponding LED among the reagent loader position LEDs 21 to 25 by updating the reagent loader LED status (step S370). Meanwhile, when the reagent container 4 is installed in S240, the processing of the control unit 19*a* proceeds to step S250.

Next, the control unit 19*a* checks whether or not the reagent disk 5 is fully occupied (step S250). Based on the check result, the control unit 19*a* determines whether or not the inside of the reagent disk 5 is fully occupied by the reagent container 4 (step S260).

When the inside of the reagent disk 5 is fully occupied by the reagent container 4 (step S260; YES), the 19*a* turns on the corresponding LED among the reagent loader position LEDs 21 to 25 in yellow by updating the reagent loader LED status (step S370). This is for illustrating that the reagent container 4 temporarily cannot be transferred into the instrument.

When it is determined that the reagent disk 5 is not fully occupied in step S260 (step S260; NO), the processing of the control unit 19*a* proceeds to step S270.

Next, the control unit 19*a* checks the analytical parameter which corresponds to the reagent container (step S270). In the step, the presence or the absence of preliminary registration of the analytical parameter which corresponds to the reagent container in the control unit 19*a* is checked, and based on the check result, the control unit 19*a* determines whether or not the analytical parameter which corresponds to the reagent container 4 is registered in the automatic analyzer 100 (step S280).

When it is determined that the analytical parameter which corresponds to the reagent container 4 is not registered in the automatic analyzer 100 (step S280; YES), the control unit 19*a* turns on the corresponding LED among the reagent loader position LEDs 21 to 25 in yellow by updating the reagent loader LED status (step S370). This is for illustrating that the reagent container temporarily cannot be transferred into the instrument. When it is determined that the analytical parameter is registered in step S280 (step S280; NO), the processing of the control unit 19*a* proceeds to step S290.

Next, the control unit 19*a* performs expiration date check of the reagent container 4 (step S290). Based on the check result, the control unit 19*a* determines whether or not the reagent container 4 has expired (step S300).

When it is determined that the reagent container 4 has expired in step S300 (step S300; YES), the control unit 19*a* turns on the corresponding LED among the reagent loader position LEDs 21 to 25 in orange by updating the reagent loader LED status (step S370). This is for illustrating that the reagent container 4 cannot be used. When it is determined that the reagent container 4 has not been expired yet in step S300 (step S300; NO), the processing of the control unit 19*a* proceeds to step S310.

Next, the control unit 19*a* performs the reagent registration situation check of the reagent container (step S310). Based on the check result, the control unit 19*a* determines whether the reagent container 4 to be a target to be transferred in is an initially input reagent or a reinput reagent (step S320).

When it is determined that the reagent container 4 to be a target to be transferred in is a reinput reagent in step S320 (step S320; YES), the processing of the control unit 19*a* proceeds to S330. In the other case (step S320; NO), that is, when the reagent container 4 is the initially input reagent, the determination of step S340 and step S350 which will be described later is not necessary, and thus, the control unit 19*a* turns on the corresponding LED among the reagent loader position LEDs 21 to 25 in green by updating the reagent loader LED status (step S370). This is for illustrating that each check is normally ended.

Next, the control unit 19*a* performs remaining volume check of the reagent container 4 (step S330). Based on the check result, the control unit 19*a* distinguishes whether or not the remaining volume of the reagent container 4 is used up (step S340).

When it is determined the remaining volume of the reagent container 4 is used up in step S340 (step S340; YES), the control unit 19*a* turns on the corresponding LED among the reagent loader position LEDs 21 to 25 in orange by updating the reagent loader LED status (step S370). This is for illustrating that the reagent container 4 cannot be used. When it is determined that the remaining volume is not used up in step S340 (step S340; NO), the processing of the control unit 19*a* proceeds to step S350.

Next, the control unit 19*a* checks whether or not four months have elapsed after the reagent container is initially registered (step S350). Based on the check result, the control unit 19*a* determines whether or not elapsed time after the initial registration of the reagent container 4 exceeds four months (step S360).

When the elapsed time after the initial registration of the reagent container 4 exceeds four months in step S360 (step S360; YES), the control unit 19*a* turns on the corresponding LED among the reagent loader position LEDs 21 to 25 in orange by updating the reagent loader LED status (step S370). This is for illustrating that the reagent container 4 cannot be used.

When it is determined that the elapsed time after the initial registration of the reagent container 4 does not exceed four months in step S360 (step S360; NO), the control unit 19*a* turns on the corresponding LED among the reagent loader position LEDs 21 to 25 in green by updating the reagent loader LED status (step S370). This is for illustrating that each check is normally ended.

Next, by using FIG. 11, a processing flow regarding the update of the reagent status information when transferring the reagent out, in the automatic analyzer 100 according to the embodiment of the present invention, will be described. FIG. 11 is a flowchart illustrating the processing regarding the update of the reagent status information when transferring the reagent out, in the automatic analyzer 100 according to the embodiment of the present invention.

When a loader switch is input by the user and the drive of the reagent loader mechanism is instructed, the control unit 19*a* drives the reagent loader mechanism to the RFID reading position 6*b* from the reagent loading position 6*a*, and performs the reagent container setting status check (step S400). Based on the check result, the control unit 19*a* determines whether or not the inverse placement of the reagent container 4 on the reagent loader position or the malfunction of the RFID reader is detected from the detection result of the sensor on position of reagent loader 20 and the reading result of the RFID antenna 30 in S410 (step S410). When the inverse placement of the reagent container 4 on the reagent loader position or the malfunction of the RFID reader is detected (step S410; YES), the control unit 19*a* turns on the corresponding LED among the reagent loader position LEDs 21 to 25 in yellow by updating the reagent loader LED status (step S430). This is for illustrating that the reagent container 4 which temporarily cannot be used is present.

Next, when NO is determined in step S410, the control unit 19*a* determines whether or not the reagent container 4 is installed, based on the result of the reagent container setting status check of step S400 (step S420).

When it is determined that the reagent container 4 is not installed (step S420; NO), the control unit 19*a* turns off the corresponding LED among the reagent loader position LEDs 21 to 25 by updating the reagent loader LED status (step S430).

When it is determined that the reagent container 4 is installed (step S420; YES), the control unit 19*a* turns on the corresponding LED among the reagent loader position LEDs 21 to 25 in green by updating the reagent loader LED status of S430 (step S430). This is for illustrating that all of the checks are normally ended.

The user can judge the reagent status of the installed reagent container at a glance, that is, at which position the reagent container is installed on the reagent loader mechanism, by seeing the display.

Next, by using FIG. 12, a processing flow regarding the control of the reagent loader position LED in the automatic analyzer 100 according to the embodiment of the present invention will be described. FIG. 12 is a flowchart illustrating the processing regarding the control of the reagent loader position LED in the automatic analyzer 100 according to the embodiment of the present invention.

As illustrated in FIG. 12, first, the control unit 19*a* reads the corresponding reagent history information from the in-loading reagent information storage unit 119*i* based on the identification information of the reagent container 4 loaded on the reagent disk 5 (step S10).

The control unit 19*a* generates the reagent status information from the corresponding reagent history information (step S20). The control unit 19*a* reads the reagent loader position information for all of the reagent loader positions from the reagent loader position information storage unit 119*j* inside the storage unit 19*d* (step S30). The control unit 19*a* generates the reagent loader position status information for all of the reagent loader positions from the reagent loader position information (step S40).

The control unit 19*a* decides the following status of each of the reagent loader position LEDs 21 to 25 based on the reagent status information and the reagent loader position status information (step S50). The control unit 19*a* determines whether or not the status of the current reagent loader position LED is the same as the decided following status (step S60).

When the determination result of step S60 is YES, the control unit 19*a* ends the processing. The reagent loader position LED maintains the current status. When the determination result of step S60 is NO, the control unit 19*a* updates the reagent loader position LED (step S70). By performing the flow at a predetermined time interval, the LED display of the reagent loader position can always be displayed in the latest status.

Next, by using FIG. 13, a processing flow illustrating a flow of the control of the switch LEDs and the switch operations when operating each switch in the automatic analyzer 100 according to the embodiment of the present invention will be described. FIG. 13 is a flowchart illustrating the processing illustrating the flow of the control of the switch LEDs and the switch operations when operating each switch in the automatic analyzer 100 according to the embodiment of the present invention.

As illustrated in FIG. 13, after the switch operation is generated, the control unit 19a obtains the instrument status information from the information storage unit of instrument status 1191 (step S110). Specifically, the instrument status information is updated by the instrument status management unit 119g.

The control unit 19a obtains the switch information from the switch information storage unit 119k (step S120). Based on the switch information obtained from the switch information storage unit 119k, the switch status management unit 119d generates switch status information (step S130). The control unit 19a decides the following status of the switch LED based on the generated switch status information (step S140).

Comparing the current switch LED status and the following switch LED status to each other, the control unit 19a determines whether or not the current switch LED status and the following switch LED status match each other (step S150). When the determination result of step S150 is YES, the control unit 19a does not update the switch LED.

When the determination result in step S150 is NO, the control unit 19a updates the switch LED (step S160). In addition, the control unit 19a determines whether or not the switch operation can be received, based on the current switch status information, the following switch status information, and the instrument status information (step S170).

Based on the determination result, the control unit 19a judges whether or not the switch operation is received (step S180). When it is determined that the switch operation is not received (step S180; YES), the control unit 19a does not perform the operation which uses the switch operation as a trigger. When it is determined that the switch operation is received (step S180; NO), the control unit 19a performs the operation which uses the switch operation as a trigger (step S190). By performing the flow at the predetermined time interval, each switch LED display can always be displayed in the latest status.

Next, operational effects of the automatic analyzer 100 according to the embodiment of the present invention will be described. In the embodiment, the LED display is updated by the reagent status information updated based on the reagent history information stored in the in-loading reagent information storage unit 119i, and the reagent loader position LED control information generated based on the reagent loader position status information updated based on the reagent loader position information stored in the reagent loader position information storage unit 119j. For this reason, the user can judge the reagent status of the reagent container 4 on the reagent loader only by the display of the reagent loader position LEDs 21 to 25 without confirming the reagent information on the screen of the display unit of the control device 19.

In addition, in the embodiment, the reagent loading switch 26 which is used in preparing the reagent and the timer reset switch 28 are disposed in the analytical module, and the timing at which the switches can be operated is respectively displayed by the reagent loading switch LED 27 and the timer reset switch LED 29. For this reason, the user can install and take out the reagent container 4 without operating the screen of the display unit of the control device 19.

As described above, according to the embodiment, operability can be improved when the user installs and takes out the reagent container while confirming the information of the reagent container. In other words, it is possible to improve usability of the user in handling the reagent container, and efficiency of preparation of the reagent.

In addition, in the embodiment, when the reagent container is transferred out of the instrument, the LED display is controlled based on the information stored in the storage unit inside the instrument, but the LED display may be controlled based on the reading result of the RFID at the RFID reading position 6b. In this case, immediately after pushing down the reagent loading switch 26, the reagent loader position LEDs 21 to 25 are turned on in green or turned off, and when the reagent loader 6 is stopped at the RFID reading position 6b, the colors of the reagent loader position LEDs 21 to 25 change to green, yellow, and orange. Accordingly, when the reagent loader 6 moves between the reagent setting position 6c and the reagent loading position 6a, it is possible to display the latest reagent status (whether or not the reagent has expired, or the like), and the reagent container status (whether or not the reagent container is inversely placed, or the like). In addition, in this case, the reading position of the RFID reader may not be the RFID reading position 6b, and may be the reagent loading position 6a, the reagent setting position 6c, or both of the reagent loading position 6a and the reagent setting position 6c.

In addition, the present invention is not limited to the above-described example, and includes various modification examples. The above-described example is for making it easy to understand the present invention, and the present invention is not necessarily limited to all of the described configurations. In addition, it is possible to replace a part of the configuration of a certain example with a configuration of another example, and to add a configuration of another example to the configuration of a certain example. In addition, a part of the configuration of each example can be added, removed, and replaced with another configuration.

Furthermore, the number of reagent containers which can be transferred in and out at one time by the reagent loader mechanism is not limited to five, and for example, the number of reagent containers may be one, or may be more than five. In addition, the reagent loader position LEDs 21 to 25 may be the display unit other than the LED, for example, a lamp. In addition, a small-sized liquid crystal screen may be provided and the information which corresponds to the LEDs 21 to 25 may be collectively displayed on one screen.

REFERENCE SIGNS LIST

1 . . . SAMPLE CONTAINER
2 . . . SAMPLE RACK
3 . . . RACK TRANSFER LINE
4 . . . REAGENT CONTAINER
4a . . . INNER BOTTLE
4b . . . INTERMEDIATE BOTTLE
4c . . . OUTER BOTTLE
4d . . . SAMPLE IDENTIFICATION LABEL
5 . . . REAGENT DISK (REAGENT CONTAINER RETAIN UNIT)
6 . . . REAGENT LOADER
6a . . . REAGENT LOADING POSITION
6b . . . RFID READING POSITION
6c . . . REAGENT SETTING POSITION
7 . . . REAGENT DISK COVER
7a . . . REAGENT DISK COVER OPENING UNIT
8 . . . REACTION CELL
9 . . . INCUBATOR DISK
10 . . . SAMPLE PIPETTING NOZZLE
11 . . . REAGENT PIPETTING NOZZLE
12 . . . REACTION CELL & SAMPLE PIPETTING TIP UNLOADING UNIT

13 ... REACTION CELL & SAMPLE PIPETTING TIP UNLOADING UNIT
15 ... DISPOSAL HOLE
16 ... TRANSFER MECHANISM
16a ... TIP ATTACHMENT POSITION
17a, 17b ... NOZZLE
18a, 18b ... DETECTION UNIT
19 ... CONTROL DEVICE
19a ... CONTROL UNIT
19d ... STORAGE UNIT
20 ... SENSOR ON POSITION OF REAGENT LOADER
21 TO 25 ... REAGENT LOADER POSITION LED
26 ... REAGENT LOADING SWITCH
27 ... REAGENT LOADING SWITCH LED
28 ... TIMER RESET SWITCH
29 ... TIMER RESET SWITCH LED
30 ... RFID ANTENNA
31 ... REAGENT UNIT COVER

The invention claimed is:

1. An automatic analyzer comprising:
a reagent container retaining unit which retains a plurality of reagent containers;
a reagent loader which has a plurality of slots into which respective reagent containers are inserted;
a sensor disposed in each slot which detects a presence or an absence of a reagent container in a respective slot;
a reader which reads identification information, from a reagent container inserted in the slot, that identifies a reagent accommodated in the reagent container inserted in the slot;
a reaction disk holding a plurality of reaction containers, one or more of the reaction containers holding a solution of a sample to be analyzed and a reagent;
a detection unit that performs detection processing of the solution for analysis of the sample;
a plurality of display areas that are disposed on the reagent container retaining unit in physical correspondence to respective slots that the display area corresponds to;
a first switch configured to instruct a control unit to move the reagent loader,
wherein the control unit includes a storage unit which stores the identification information and reagent status information indicating a status of each of the reagents accommodated in each of the reagent containers,
wherein the control unit is connected to the reagent container retaining unit, the reagent loader, the sensor, the reader, the reaction disk, the detection unit, the plurality of display areas, and the first switch,
wherein the control unit is programmed to:
control the reagent loader to move to different positions in a vertical direction with respect to the reagent disk,
receive an input from the sensor indicating the presence or absence of a reagent container in a slot,
control the reader to read identification information from a reagent container inserted in a slot and send a read result to the control unit,
control each display area to independently indicate, based on the position of the reagent loader in the vertical direction, a presence or an absence of a reagent container in the corresponding slot, a status of a reagent accommodated in a reagent container inserted into the corresponding slot, and a status of the corresponding slot,
wherein the status of a slot is based on at least one of the input of the sensor, whether the reagent container retaining unit is fully occupied, and whether there is a malfunction of reading the identification information,
wherein the presence or absence of a reagent container in a corresponding slot is based on one of the read result of the reader and the input from the sensor, and
wherein the status of a reagent is based on the reagent status information corresponding to the reagent identified by the identification information read by the reader.

2. The automatic analyzer according to claim 1, wherein the control unit is further programmed to move the reagent loader in the vertical direction to a first position, and
wherein the reagent container retaining unit is sealed from outside air when the reagent loader is in the first position.

3. The automatic analyzer according to claim 2, wherein the control unit is further programmed to measure an elapsed time from when the reagent loader is moved from the first position, and
control the reagent loader to move the reagent loader to the first position when the elapsed time exceeds a first threshold value.

4. The automatic analyzer according to claim 3, further comprising:
a first indicator,
wherein the control unit is further programmed to control the first indicator to indicate that the reagent loader moves to the first position when the elapsed time exceeds a second threshold value of time, which is less than the first threshold value.

5. The automatic analyzer according to claim 4, further comprising:
a second switch which instructs the control unit to reset the measured elapsed time.

6. The automatic analyzer according to claim 5, further comprising:
a second indicator indicating whether or not the switching of an ON/OFF status of the first switch can be received by the control unit.

7. The automatic analyzer according to claim 1, wherein each of the display areas is a light emitting diode.

8. The automatic analyzer according to claim 1, wherein the status of the reagent accommodated by the reagent container inserted into the slot indicated by the corresponding display area is one of the reagent can be used for analysis of a sample, the reagent temporarily cannot be used for analysis of a sample, and the reagent cannot be used for analysis of a sample.

9. An automatic analyzer comprising:
a reagent container retaining unit which retains a plurality of reagent containers;
a reagent loader which has a plurality of slots into which respective reagent containers are inserted;
a sensor disposed in each slot which detects a presence or an absence of a reagent container in a respective slot;
a reader which reads identification information, from a reagent container inserted in the slot, that identifies a reagent accommodated in the reagent container inserted in the slot;
a reaction disk holding a plurality of reaction containers, one or more of the reaction containers holding a solution of a sample to be analyzed and a reagent;
a detection unit that performs detection processing of the solution for analysis of the sample;
a plurality of display areas that are disposed on the reagent container retaining unit in physical correspondence to respective slots that the display area corresponds to;

a first switch configured to instruct a control unit to move the reagent loader, wherein the control unit includes a storage unit which stores the identification information and reagent status information indicating a status of each of the reagents accommodated in each of the reagent containers, wherein the control unit is connected to the reagent container retaining unit, the reagent loader, the sensor, the reader, the reaction disk, the detection unit, the plurality of display areas, and the first switch, wherein the control unit is programmed to:

control the reagent loader to move in a vertical direction with respect to the reagent disk to a first position allowing a reagent container to be inserted into a slot, control the reagent loader to move vertically to a second position, which is different from the first position, and at the second position: control the reader to read identification information from a reagent container inserted in a slot and send a read result to the control unit, and control a display area corresponding to the slot having the inserted regent container from which the information was read to indicate a status of a reagent accommodated in the inserted reagent container based on the reagent status information corresponding to the reagent identified by the identification information read by the reader, control the reagent loader to move vertically to a third position, which is different from the first position and the second position, and at the third position, receive an input from a sensor indicating the presence or absence of a reagent container in a slot and control a display area corresponding to the slot to indicate the presence or absence of a reagent container based on the input from the sensor, wherein, in the vertical direction, the first position is lowest and the third position is the highest position among the first, second and third positions.

10. The automatic analyzer according to claim 9, wherein the reagent container retaining unit is sealed from outside air when the reagent loader is in the first position.

11. The automatic analyzer according to claim 10, wherein the control unit is further programmed to measure an elapsed time from when the reagent loader is moved from the first position, and control the reagent loader to move the reagent loader to the first position when the elapsed time exceeds a first threshold value.

12. The automatic analyzer according to claim 11, further comprising:
a first indicator,
wherein the control unit is further programmed to control the first indicator to indicate that the reagent loader moves to the first position when the elapsed time exceeds a second threshold value of time, which is less than the first threshold value.

13. The automatic analyzer according to claim 12, further comprising:
a second switch which instructs the control unit to reset the measured elapsed time.

14. The automatic analyzer according to claim 13, further comprising:
a second indicator indicating whether or not the switching of an ON/OFF status of the first switch can be received by the control unit.

15. The automatic analyzer according to claim 9, wherein each of the display areas is a light emitting diode.

16. The automatic analyzer according to claim 9, wherein the status of the reagent accommodated by the reagent container inserted into the slot indicated by the corresponding display area is one of the reagent can be used for analysis of a sample, the reagent temporarily cannot be used for analysis of a sample, and the reagent cannot be used for analysis of a sample.

17. An automatic analyzer comprising:
a reagent container retaining unit which retains a plurality of reagent containers;
a reagent loader which has a plurality of slots into which respective reagent containers are inserted;
a sensor which detects a presence or an absence of a reagent container in each slot;
a reader which reads identification information, from a reagent container inserted in the slot, that identifies a reagent accommodated in the reagent container inserted in the slot;
a reaction disk holding a plurality of reaction containers, one or more of the reaction containers holding a solution of a sample to be analyzed and a reagent;
a detection unit that performs detection processing of the solution for analysis of the sample;
a plurality of display areas that are disposed on the reagent container retaining unit in physical correspondence to respective slots that the display area corresponds to;
a first switch configured to instruct a control unit to move the reagent loader,
wherein the control unit includes a storage unit which stores the identification information and reagent status information indicating a status of each of the reagents accommodated in each of the reagent containers,
wherein the control unit is connected to the reagent container retaining unit, the reagent loader, the sensor, the reader, the reaction disk, the detection unit, the plurality of displays, and the first switch,
wherein the control unit is programmed to:
if the first switch instructs the control unit to move the reagent loader, control the reagent loader to move in a vertical direction with respect to the reagent disk to a first position allowing a reagent container to be inserted into a slot,
receive an input from the sensor indicating the presence or absence of a reagent container in a slot,
control the reader to read identification information from a reagent container inserted in a slot and send a read result to the control unit,
control each display area to independently indicate a status of a reagent accommodated in a reagent container inserted into the corresponding slot based on the reagent status information corresponding to the reagent identified by the identification information read by the reader,
wherein the status of the reagent accommodated by the reagent container inserted into the slot indicated by the corresponding display area is one of the reagent can be used for analysis of a sample, the reagent temporarily cannot be used for analysis of a sample, and the reagent cannot be used for analysis of a sample.

* * * * *